(12) United States Patent
Argentine et al.

(10) Patent No.: US 10,111,742 B2
(45) Date of Patent: Oct. 30, 2018

(54) STENT-GRAFT HAVING SUPPORTED TRANSITION STENT AND METHOD

(71) Applicant: Medtronic Vascular, Inc., Santa Rosa, CA (US)

(72) Inventors: Jeffery Argentine, Petaluma, CA (US); Benjamin Wolf, Santa Rosa, CA (US); Ana Zavala, Santa Rosa, CA (US)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 69 days.

(21) Appl. No.: 15/266,283

(22) Filed: Sep. 15, 2016

(65) Prior Publication Data

US 2018/0071077 A1    Mar. 15, 2018

(51) Int. Cl.
*A61F 2/07* (2013.01)
*A61F 2/954* (2013.01)
*A61F 2/06* (2013.01)
*A61F 2/89* (2013.01)

(52) U.S. Cl.
CPC ............... *A61F 2/07* (2013.01); *A61F 2/89* (2013.01); *A61F 2002/065* (2013.01); *A61F 2002/075* (2013.01); *A61F 2220/005* (2013.01); *A61F 2220/0075* (2013.01)

(58) Field of Classification Search
CPC ........ A61F 2/07; A61F 2002/0065–2002/0067
USPC ................................................ 623/1.35–1.38
See application file for complete search history.

(56) References Cited

U.S. PATENT DOCUMENTS

| 6,576,007 | B2* | 6/2003 | Dehdashtian | A61F 2/07 623/1.13 |
|---|---|---|---|---|
| 8,192,482 | B2* | 6/2012 | Goicoechea | A61F 2/07 623/1.16 |
| 2004/0098086 | A1* | 5/2004 | Goicoechea | A61F 2/82 623/1.11 |
| 2004/0098115 | A1* | 5/2004 | Goicoechea | A61F 2/82 623/1.35 |
| 2008/0015682 | A1* | 1/2008 | Majercak | A61B 17/12022 623/1.13 |
| 2010/0100168 | A1* | 4/2010 | Chuter | A61F 2/07 623/1.13 |
| 2013/0123904 | A1* | 5/2013 | Cragg | A61F 2/82 623/1.16 |
| 2015/0157446 | A1* | 6/2015 | Kelly | A61F 2/07 623/1.11 |
| 2015/0157448 | A1* | 6/2015 | Kelly | A61F 2/07 623/1.11 |
| 2015/0320578 | A1* | 11/2015 | Bui | A61F 2/07 623/1.35 |
| 2016/0367387 | A1* | 12/2016 | Golden | A61F 2/885 |
| 2017/0296324 | A1* | 10/2017 | Argentine | A61F 2/07 |

(Continued)

*Primary Examiner* — Suzette J Gherbi

(57) ABSTRACT

A stent-graft includes a graft material having a main body, a first leg, a second leg, and a transition region where the first leg and the second leg meet the main body. A main body transition stent is coupled to the main body. A transition stent support including a gusset is coupled to the graft material such that a transition apex of the main body transition stent is interposed between the gusset and the graft material, the transition apex being aligned with the transition region. The transition apex, which is susceptible to failure, is stabilized by the gusset in combination with a supporting ligament. The gusset and supporting ligament prevent flexing of the transition apex and the associated failure thereof.

16 Claims, 3 Drawing Sheets

(56) References Cited

U.S. PATENT DOCUMENTS

2018/0021155 A1* 1/2018 Hadley ............... A61F 2/89
2018/0116783 A1* 5/2018 Kratzberg ............ A61F 2/07

* cited by examiner

STENT-GRAFT HAVING SUPPORTED TRANSITION STENT AND METHOD

BACKGROUND

Field

The present application relates to an intra-vascular device and method. More particularly, the present application relates to a device for treatment of intra-vascular diseases.

Description of the Related Art

A conventional bifurcated stent-graft typically includes a radially expandable reinforcement structure, formed from a plurality of annular stent rings, and a cylindrically shaped bifurcated layer of graft material defining lumens to which the stent rings are coupled. Bifurcated stent-grafts are well known for use in human vessels.

To illustrate, endovascular aneurysmal exclusion is a method of using a bifurcated stent-graft to exclude pressurized fluid flow from the interior of an aneurysm, thereby reducing the risk of rupture of the aneurysm and the associated invasive surgical intervention. However, the bifurcated stent-graft is constantly being subjected to external forces, e.g., due to the pressurized fluid flow. This external force can cause the bifurcated stent-graft to fail over time.

SUMMARY

A stent-graft includes a graft material having a main body, a first leg, a second leg, and a transition region where the first leg and the second leg meet the main body. A main body transition stent is coupled to the main body. A transition stent support including a gusset is coupled to the graft material such that a transition apex of the main body transition stent is interposed between the gusset and the graft material, the transition apex being aligned with the transition region. The transition apex, which is susceptible to failure, is stabilized by the gusset in combination with a supporting ligament. The gusset and supporting ligament prevent flexing of the transition apex and the associated failure thereof.

These and other features in accordance with various embodiments will be more readily apparent from the detailed description set forth below taken in conjunction with the accompanying drawings.

BRIEF DESCRIPTION OF DRAWINGS

Common reference numerals are used throughout the drawings and detailed description to indicate like elements.

DETAILED DESCRIPTION

Figure 1:
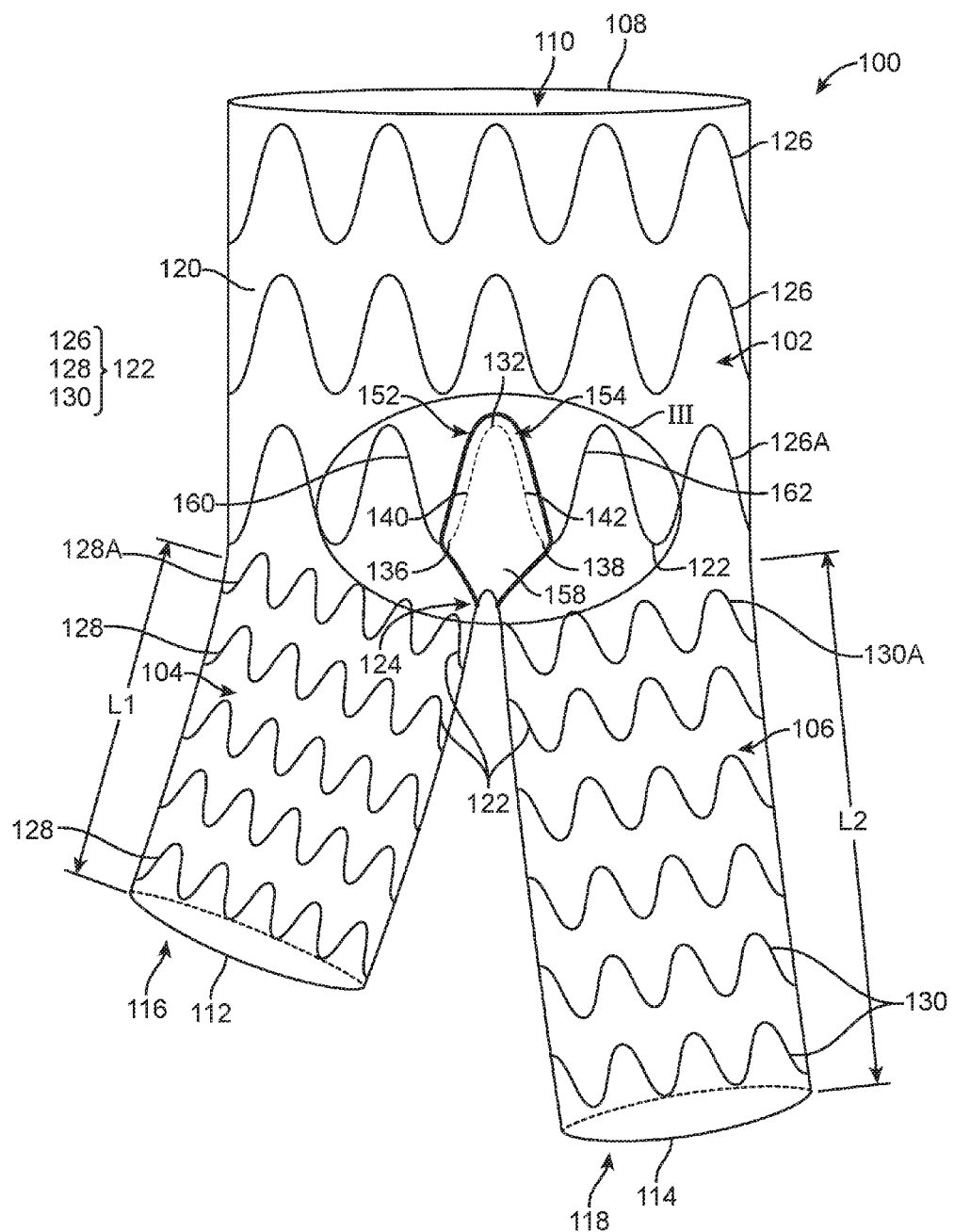
FIG. 1 is an anterior perspective view of a bifurcated stent-graft in accordance with one embodiment.
Figure 2:
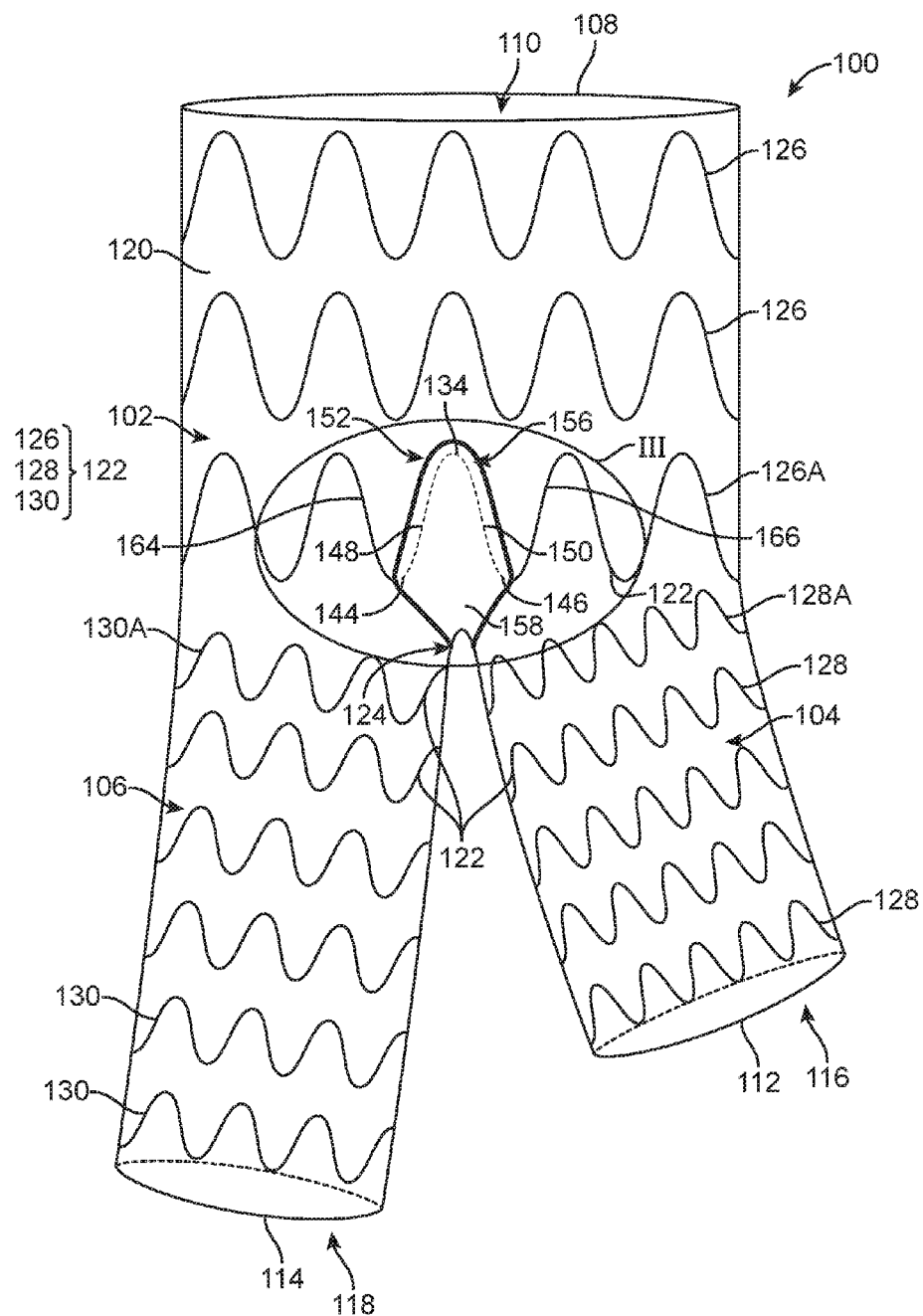
FIG. 2 is a posterior perspective view of the bifurcated stent-graft of FIG. 1 in accordance with one embodiment.

FIG. 1 is an anterior perspective view of a bifurcated stent-graft 100, e.g., an aortic bifurcated stent-graft, in accordance with one embodiment. FIG. 2 is a posterior perspective view of bifurcated stent-graft 100 of FIG. 1 in accordance with one embodiment. Referring now to FIGS. 1 and 2 together, bifurcated stent-graft 100 includes a main body 102, a short, e.g., first, leg 104, and a long, e.g., second, leg 106.

Main body 102 extends from a proximal end 108 of bifurcated stent-graft 100 to legs 104, 106. Main body 102 defines a main lumen 110. Short leg 104 extends from main body 102 to a distal end 112 of short 104. Long leg 106 extends from main body 102 to a distal end 114 of long leg 106. Legs 104, 106 define branch lumens 116, 118, respectively. Main lumen 110 is bifurcated into branch lumens 116, 118.

As used herein, the proximal end of a prosthesis such as bifurcated stent-graft 100 is the end closest to the heart via the path of blood flow whereas the distal end is the end furthest away from the heart during deployment. In contrast and of note, the distal end of the catheter is usually identified to the end that is farthest from the operator (handle) while the proximal end of the catheter is the end nearest the operator (handle). However, those of skill in the art will understand that depending upon the access location, the stent-graft and delivery system description may be consistent or opposite in actual usage.

Bifurcated stent-graft 100 includes graft material 120 and stents 122, sometimes called stent rings 122, coupled to graft material 120. At main body 102, graft material 120 is cylindrical having a substantially uniform diameter. Similarly, at short leg 104, graft material 120 is cylindrical. Further, at long leg 106, graft material 120 is cylindrical. However, in other embodiments, graft material 120 varies in diameter at one or more of main body 102, short leg 104, and long leg 106.

In one embodiment, graft material 120 is non-permeable, e.g., is polyester terephthalate (PET), expanded polyester terephthalate (ePET), or other non-permeable graft material. As graft material 120 is non-permeable, blood or other fluid does not pass through graft material 120.

A transition region 124 is defined at the intersection of main body 102, short leg 104, and long leg 106. Transition region 124 is sometimes called the crotch of bifurcated stent-graft 100.

Stents 122 include main body stents 126, short leg stents 128, and long leg stents 130, sometimes called main body stent rings 126, short leg stent rings 128, and long leg stent rings 130, respectively. Illustratively, stents 122 are self-expanding structures, e.g., formed of nickel titanium alloy (nitinol), or other shaped memory material. Stents 122 are attached to graft material 120 with an attachment structure, for example, stitching, adhesive, or other attachment means in various embodiments.

Main body stents 126 are coupled to main body 102. Main body stents 126 include a main body transition stent 126A at transition region 124. More particularly, main body transition stent 126A is the most distal of main body stents 126 and directly adjacent short leg 104 and long leg 106.

Short leg stents 128 are coupled to short leg 104. Short leg stents 128 include a short leg transition stent 128A, sometimes called a first leg transition stent 128A, adjacent main body 102. More particularly, short leg transition stent 128A is the most proximal of short leg stents 128 and directly adjacent main body transition stent 126A.

Long leg stents 130 are coupled to long leg 106. Long leg stents 130 include a long leg transition stent 130A, sometimes called a second leg transition stent 130A, adjacent main body 102. More particularly, long leg transition stent 130A is the most proximal of long leg stents 130 and directly adjacent main body transition stent 126A.

A length L1 of short leg 104 is less than a length L2 of long leg 106. Although FIG. 1 is referred to as an anterior perspective view and FIG. 2 is referred to as a posterior perspective view, the views are not limiting. For example, FIG. 1 can be a posterior perspective view and FIG. 2 can be an anterior perspective view. Generally, providing short leg 104 and long leg 106 with different lengths L1, L2 provides a mode of adjustment of bifurcated stent-graft 100 to accommodate variations in anatomy. In another embodiment, short leg 104 and long leg 106 have the same length. For clarity of description, the view of FIG. 1 and features therein shall be referred to as anterior and the view of FIG. 2 and features therein shall be referred to as posterior. However, in light of this disclosure, those of skill in the art will understand that the terms "anterior" and "posterior" may be reversed depending upon the particular deployment of bifurcated stent-graft 100.

Main body transition stent 126A includes an anterior transition apex 132 and a posterior transition apex 134 both aligned with transition region 124. Anterior transition apex 132 is directly opposite posterior transition apex 134 on main body 102.

In one embodiment, bifurcated stent-graft 100 is deployed to exclude pressurized fluid flow from the interior of an aneurysm, thereby reducing the risk of rupture of the aneurysm and the associated invasive surgical intervention. However, bifurcated stent-graft 100 is constantly being subjected to external forces, e.g., due to the pressurized fluid flow. This external force is concentrated at transition region 124 and at transition apexes 132, 134. More particularly, repeated flexing of apexes 132, 134 is undesirable and can cause main body transition stent 126A to fail (break) at apexes 132, 134. As described below and in accordance with one embodiment, apexes 132, 134 are supported and prevented from failing.

Paying particular attention now to FIG. 1, main body transition stent 126A further includes a first anterior leg apex 136, a second anterior leg apex 138, a first anterior transition strut 140, and a second anterior transition strut 142. First anterior leg apex 136 is adjacent short leg 104 and second anterior leg apex 138 is adjacent long leg 106. First anterior transition strut 140 extends from first anterior leg apex 136 to anterior transition apex 132. Second anterior transition strut 142 extends from second anterior leg apex 138 to anterior transition apex 132.

Paying particular attention now to FIG. 2, main body transition stent 126A further includes a first posterior leg apex 144, a second posterior leg apex 146, a first posterior transition strut 148, and a second posterior transition strut 150. First posterior leg apex 144 is adjacent long leg 106 and second posterior leg apex 146 is adjacent short leg 104. First posterior transition strut 148 extends from first posterior leg apex 144 to posterior transition apex 134. Second posterior transition strut 150 extends from second posterior leg apex 146 to posterior transition apex 134.

Referring again to FIGS. 1 and 2 together, bifurcated stent-graft 100 further includes a transition stent support 152. Transition stent support 152 supports and isolates main body transition stent 126A. In one embodiment, transition stent support 152 is a graft material, e.g., similar to graft material 130. Transition stent support 152 is attached to graft material 130 with an attachment structure, for example, stitching, adhesive, or other attachment means in various embodiments.

Transition stent support 152 includes an anterior, first, gusset 154, a posterior, second, gusset 156, and a transition region support 158. Gussets 154, 156 are sometimes called patches. Transition region support 158 extends from anterior gusset 154 over transition region 124 to posterior gusset 156.

Anterior gusset 154 is triangular shaped. Anterior gusset 154 covers anterior transition apex 132, first anterior leg apex 136, second anterior leg apex 138, first anterior transition strut 140, and second anterior transition strut 142. More particularly, anterior transition apex 132, first anterior leg apex 136, second anterior leg apex 138, first anterior transition strut 140, and second anterior transition strut 142 and interposed between, sometimes called sandwiched or encapsulated by, anterior gusset 154 and graft material 120.

Anterior gusset 154 stabilizes and support anterior transition apex 132, first anterior leg apex 136, second anterior leg apex 138, first anterior transition strut 140, and second anterior transition strut 142. In this manner, anterior gusset 154 prevents repeated flexing of anterior transition apex 132 and failure thereof.

A third anterior transition strut 160 extends from first anterior leg apex 136 and a fourth anterior transition strut 162 extends from second anterior leg apex 138. Third anterior transition strut 160 and fourth anterior transition strut 162 are uncovered by and exposed from anterior gusset 154.

Similarly, posterior gusset 156 stabilizes and support posterior transition apex 134, first posterior leg apex 144, second posterior leg apex 146, first posterior transition strut 148, and second posterior transition strut 150. In this manner, posterior gusset 156 prevents repeated flexing of posterior transition apex 134 and failure thereof.

A third posterior transition strut 164 extends from first posterior leg apex 144 and a fourth posterior transition strut 166 extends from second posterior leg apex 146. Third posterior transition strut 164 and fourth posterior transition strut 166 are uncovered by and exposed from posterior gusset 156.

Figure 3:
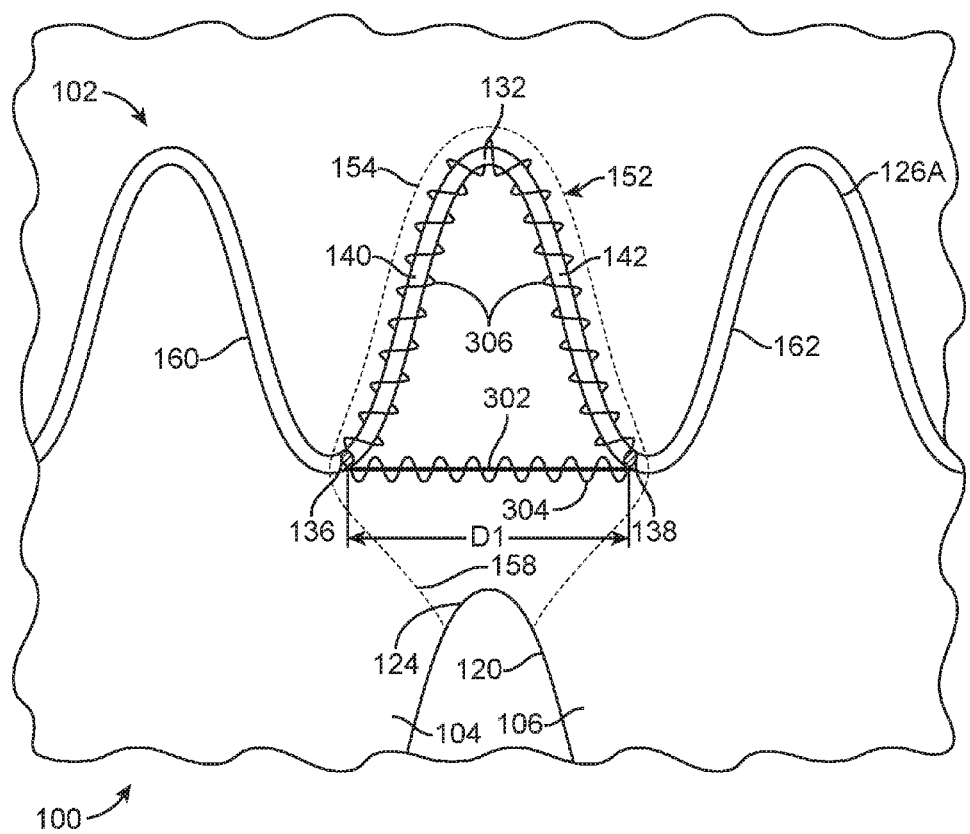
FIG. 3 is an enlarged plan view of a region III of the bifurcated stent-graft of FIG. 1 in accordance with one embodiment.

FIG. 3 is an enlarged plan view of a region III of bifurcated stent-graft 100 of FIG. 1 in accordance with one embodiment. In FIG. 3, anterior gusset 154 is indicated in a dashed line to allow visualization of features covered by anterior gusset 154.

Referring now to FIG. 3, bifurcated stent-graft 100 further includes an anterior supporting ligament 302. Anterior supporting ligament 302 is a linear element, e.g., a thread, rod, or other supporting member.

Anterior supporting ligament 302 is connected to and extends between first anterior leg apex 136 and second anterior leg apex 138. Stated another way, first and second anterior leg apexes 136, 138 adjacent to anterior transition apex 132 are connected together with anterior supporting ligament 302. Anterior supporting ligament 302 prevents first anterior leg apex 136 from moving away from second anterior leg apex 138, i.e., maintains a fixed distance D1 between first anterior leg apex 136 and second anterior leg apex 138. By preventing relative motion between first anterior leg apex 136 and second anterior leg apex 138, anterior supporting ligament 302 prevents flexing of anterior transition apex 132 and the associated failure thereof.

In one embodiment, anterior supporting ligament 302 is attached to graft material 120 and/or anterior gusset 154 by an anterior attachment structure 304, e.g., stitching. This stabilizes anterior supporting ligament 302 thus enhancing the stabilization of first anterior leg apex 136 relative to second anterior leg apex 138. In one embodiment, an anterior attachment structure 306, e.g., stitching, attaches anterior gusset 154 to graft material 120 and extends around first anterior transition strut 140, anterior transition apex 132, and second anterior transition strut 142. Anterior attachment structure 304 and anterior attachment structure 306 can be separate stitching or regions of a common stitch.

Although FIG. 3 is described in relation to the region III of FIG. 1, the discussion is equally applicable to the region III of FIG. 2. More particularly, the discussion is in relation to the region III of FIG. 1 of anterior supporting ligament 302, first anterior leg apex 136, second anterior leg apex 138, anterior transition apex 132, anterior attachment structure 304, and anterior attachment structure 306 is equally applicable to the region III of FIG. 2 including a posterior supporting ligament, first posterior leg apex 144, second posterior leg apex 146, posterior transition apex 134, a posterior attachment structure, and a posterior attachment structure, respectively.

This disclosure provides exemplary embodiments. The scope is not limited by these exemplary embodiments. Numerous variations, whether explicitly provided for by the specification or implied by the specification or not, such as variations in structure, dimension, type of material and manufacturing process may be implemented by one of skill in the art in view of this disclosure.

What is claimed is:

1. A stent-graft comprising:
   a graft material comprising:
      a main body;
      a first leg;
      a second leg; and
      a transition region where the first leg and the second leg meet the main body;
   a main body transition stent coupled to the main body;
   a transition stent support coupled to the graft material, a transition apex of the main body transition stent being interposed between the transition stent support and the graft material, the transition apex being aligned with the transition region; and
   a first leg transition stent coupled to the first leg directly adjacent to the main body transition stent.

2. The stent-graft of claim 1 wherein the main body transition stent further comprises:
   a first leg apex adjacent the first leg; and
   a second leg apex adjacent the second leg, the transition apex being between the first leg apex and the second leg apex.

3. The stent-graft of claim 2 wherein the first leg apex and the second leg apex are interposed between the transition stent support and the graft material.

4. A stent-graft comprising:
   a graft material comprising:
      a main body;
      a first leg;
      a second leg; and
      a transition region where the first leg and the second leg meet the main body;
   a main body transition stent coupled to the main body; and
   a transition stent support coupled to the graft material, a transition apex of the main body transition stent being interposed between the transition stent support and the graft material, the transition apex being aligned with the transition region, wherein the main body transition stent further comprises:
      a first leg apex adjacent the first leg;
      a second leg apex adjacent the second leg, the transition apex being between the first leg apex and the second leg apex;
      a first transition strut extending from the first leg apex to the transition apex; and
      a second transition strut extending from the second leg apex to the transition apex.

5. The stent-graft of claim 4 wherein the first transition strut and the second transition strut are interposed between the transition stent support and the graft material.

6. The stent-graft of claim 4 wherein the main body transition stent further comprises:
   a third transition strut extending from the first leg apex; and
   a fourth transition strut extending from the second leg apex, the third transition strut and the fourth transition strut being exposed from the transition stent support.

7. A stent-graft comprising:
   a graft material comprising:
      a main body;
      a first leg;
      a second leg; and
      a transition region where the first leg and the second leg meet the main body;
   a main body transition stent coupled to the main body;
   a transition stent support coupled to the graft material, a transition apex of the main body transition stent being interposed between the transition stent support and the graft material, the transition apex being aligned with the transition region, wherein the main body transition stent further comprises:
      a first leg apex adjacent the first leg;
      a second leg apex adjacent the second leg, the transition apex being between the first leg apex and the second leg apex; and
   a supporting ligament coupling the first leg apex to the second leg apex.

8. The stent-graft of claim 7 further comprising stitching coupling the supporting ligament to the graft material.

9. The stent-graft of claim 1 further comprising an attachment structure coupling the transition stent support to the graft material.

10. The stent-graft of claim 9 wherein the attachment structure comprises stitching.

11. The stent-graft of claim 1 further comprising a second leg transition stent coupled to the second leg directly adjacent to the main body transition stent.

12. A stent-graft comprising:
   a graft material comprising:
      a main body;
      a first leg;
      a second leg; and
      a transition region where the first leg and the second leg meet the main body;
   a main body transition stent coupled to the main body; and
   a transition stent support coupled to the graft material, the transition stent support comprising:
      a first gusset covering an anterior transition apex of the main body transition stent;
      a second gusset covering a posterior transition apex of the main transition stent; and
      a transition region support extending from the first gusset over the transition region to the second gusset.

13. The stent-graft of claim 12 wherein the posterior transition apex is directly opposite on the main body from the anterior transition apex.

14. The stent-graft of claim 12 wherein the first gusset and the second gusset are triangular shaped.

15. The stent-graft of claim 12 wherein the main body transition stent further comprises:
   a first anterior leg apex adjacent the first leg;
   a second anterior leg apex adjacent the second leg;

a first anterior transition strut extending from the first anterior leg apex to the anterior transition apex; and a second anterior transition strut extending from the second anterior leg apex to the anterior transition apex, wherein the first anterior leg apex, the second anterior leg apex, the first anterior transition strut and the second anterior transition strut are covered by the first gusset.

16. The stent-graft of claim 15 further comprising an anterior supporting ligament coupling the first anterior leg apex to the second anterior leg apex.

* * * * *